United States Patent [19]
Lorenz et al.

[11] Patent Number: 5,288,916
[45] Date of Patent: Feb. 22, 1994

[54] ENANTIOMERIC RESOLUTION OF 4-(3,4-DICHLOROPHENYL)-3,4-DIHYDRO-1(2H)-NAPHTHALENONE

[75] Inventors: Douglas A. Lorenz; Daniel J. Brose, both of Bend, Oreg.

[73] Assignee: Bend Research, Inc., Bend, Oreg.

[21] Appl. No.: 36,809

[22] Filed: Mar. 25, 1993

[51] Int. Cl.$^5$ ............................................. C07C 45/79
[52] U.S. Cl. .................................................. 568/324
[58] Field of Search ........................................ 568/324

[56] References Cited

U.S. PATENT DOCUMENTS 4,536,518  8/1985  Welch ................................. 514/647

OTHER PUBLICATIONS

Jin et al, Chirality, vol. 1, p. 137 (1989).

Benschop et al, Chem. Commun., pp. 1431–1432 (1970).

*Primary Examiner*—James H. Reamer
*Attorney, Agent, or Firm*—Chernoff, Vilhauer, McClung & Stenzel

[57] ABSTRACT

There is disclosed a method of separating enantiomers of 4-(3',4'-dichlorophenyl)-3,4-dihydro-1(2H)-naphthalenone comprising contacting the same with a homogeneous or nonhomogeneous liquid mixture of solvent and water, the mixture containing substantially pure and unsupported gamma-cyclodextrin or its derivatives. Also disclosed are methods of further enantiomerically enriching solid mixtures obtained from the enantiomer separation method and further extracting one enantiomer by solvent extraction of the solid mixtures obtained.

19 Claims, No Drawings

ENANTIOMERIC RESOLUTION OF 4-(3,4-DICHLOROPHENYL)-3,4-DIHYDRO-1(2H)-NAPHTHALENONE

BACKGROUND OF THE INVENTION

The cyclic ketone 4-(3,4-dichlorophenyl)-3,4-dihydro-1-(2H)-naphthalenone (hereinafter referred to as "DCPN") is an important precursor in the formulation of an anti-depressant drug. See U.S. Pat. No. 4,536,518. Enantiomeric resolution of this precursor from racemic mixtures is currently limited to analytical scale chromatography. However, there is no known process for large scale, economical separation of DCPN.

The use of cyclodextrins for enantiomeric resolution of racemic mixtures of various optically active compounds is known. See, for example, Jin et al., 1 Chirality 137 (1989), which discloses the formation of cyclodextrin crystalline inclusion complexes of racemic 1-dimethylaminonaphthalene-5-sulfonyl [dansyl] amino acids in aqueous solutions of cyclodextrin, followed by precipitation of the complex by pH adjustment, and by selective recrystallization. However, such a process is suitable only for the separation of enantiomers, such as amino acids, that have water-ionizable acid groups that may be rendered insoluble by the protonation which occurs in an acidic pH range. Benschop et al., in Chemical Communications, pp 1431–1432 (1970), disclose the partial resolution of the liquid enantiomer isopropyl methyl phosphinate using beta-cyclodextrin complex formation as one of the steps in the resolution. The beta-cyclodextrin was suspended in the liquid phosphinate and a trace amount of water was added, causing the suspension to solidify into a crystalline mass. After 24 hours, the crystalline mass was washed with ether, with the ethereal phase containing the (+)-enantiomer 17% enriched in optical purity. Such a partial resolution has little practical value, however.

In general, no method has been devised in the art of enantiomeric resolution to predict those chiral moieties that may be resolved by complexation with cyclodextrins, let alone any specific methodology having universal application.

SUMMARY OF THE INVENTION

There are essentially three aspects to the present invention. One aspect comprises a method for the separation of enantiomers of DCPN comprising the steps of contacting the enantiomers thereof with a liquid mixture of water and a solvent, the liquid mixture containing substantially pure and unsupported gamma cyclodextrin or low solubility derivatives thereof ($\gamma$-CD), thereby selectively binding one of the enantiomers to the $\gamma$-CD, and separating the enantiomers-$\gamma$-CD complex from the liquid mixture wherein the enantiomers are soluble in the liquid mixture to at least 1.0 mM and the solvent is selected so as to render the $\gamma$-CD substantially insoluble in the liquid mixture. A second aspect comprises an intermediate product of the method, namely, the DCPN enantiomers-$\gamma$-CD complex that is formed. The third aspect comprises a method of recovering one enantiomer of DCPN by solvent extraction treatment of the enantiomers-$\gamma$-CD complex obtained as a product of the method first mentioned.

DETAILED DESCRIPTION OF THE INVENTION

According to the present invention there are provided a number of simple and effective methods of resolving enantiomers of DCPN that rely upon an adjustment of the partition coefficient of the enantiomer between a solid $\gamma$-CD phase and a liquid phase. Although $\gamma$-CD is normally soluble in water, by the addition of an appropriate organic solvent, it becomes insoluble in a liquid mixture of the water and solvent, thereby forming a solid phase for selective adsorption of one enantiomeric form in preference to the other enantiomeric form in a mixture of enantiomers of DCPN. By "selective adsorption" is meant not 100% selectivity, but rather relative selectivity, whereby relatively more of one enantiomer is bound to the $\gamma$-CD. Because the mixture of enantiomers is soluble in the liquid mixture, that portion of the enantiomeric mixture that is not adsorbed by the solid $\gamma$-CD remains in the solvent, thereby effecting a degree of separation. Of the enantiomeric forms that are adsorbed by the $\gamma$-CD, the one exhibiting the greater degree of adsorption may be recovered by solvent extraction after separating the solid DCPN enantiomers-$\gamma$-CD complex from the liquid phase.

Derivatives of $\gamma$-CD that are preferred as a binding agent include anionic poly-$\gamma$-cyclodextrin; (2-hydroxypropyl)-$\gamma$-cyclodextrin; $\gamma$-cyclodextrin phosphate sodium salt; succinylated-$\gamma$-cyclodextrin; octakis (2,3,6-tri-O-acetyl)-$\gamma$-cyclodextrin; carboxymethyl-$\gamma$-cyclodextrin.

Such recovery of the DCPN enantiomers-$\gamma$-CD complex in solid form is advantageous both for purposes of recovery by conventional methods such as recrystallization and solvent extraction, and for purposes of enantiomeric enrichment of DCPN using staged operations. The term "enantiomeric enrichment" refers to the increase in the amount of one enantiomer as compared to the other. Enantiomeric enrichment may be effected by an increase or a decrease in the amount of one chiral form as compared to the other. A convenient method of expressing enantiomeric enrichment uses the concept of enantiomeric excess ("ee"), expressed by $$\% \, ee = \frac{[E1 - E2]}{[E1 + E2]} \times 100$$

wherein E1 is the amount of the first chiral form and E2 is amount of the second chiral form. Thus, if the initial ratio of the two chiral forms E1 and E2 is 50:50, as in a racemic mixture, and an enantiomeric enrichment is achieved that is sufficient to produce a final E1 to E2 ratio of 75:25, the ee with respect to the first chiral form would be 50%, calculated as $$\% \, ee = \frac{[75 - 25]}{[75 + 25]} \times 100 = 50$$

Because of its usefulness in further enantiomeric enrichment, the enantiomers-$\gamma$-CD complex is seen to be useful in its own right. A preferred composition for the complex that lends it such utility is one wherein the ratio of enantiomer to $\gamma$-CD is from 0.01 to 1.0, and the degree of enrichment in the (−)-enantiomers is from 1 to 99%. By employment of multiple stages, the extent of enantiomeric resolution may be further enhanced. Such stages may be part of a fixed bed operation or part of either an actual countercurrent operation or part of a simulated countercurrent operation.

The water and solvent liquid phase may be homogeneous or nonhomogeneous. In the case of homogeneous liquid mixtures, the solvent may be miscible or immiscible with water; in the latter case, water must be present in a concentration less than or equal to its saturation concentration in the solvent. In the case of nonhomogeneous liquid mixtures, water must be present in a concentration greater than its saturation concentration in the solvent.

Contact between the enantiomeric mixture of DCPN and the γ-CD-containing liquid mixture is preferably conducted or enhanced by agitation, which may be in the form of stirring, shaking or sonication. Separation of the γ-CD-enantiomers complex (containing relatively more of one of the enantiomeric forms bound to γ-CD) may be effected by filtration, decantation or centrifugation.

Selection of the type and amount of the organic solvent of the water/solvent liquid mixture is an important aspect of the present invention. The enantiomeric mixture must be soluble in the solvent to at least 1.0 mM, and the solvent must render the γ-CD substantially insoluble in the water/solvent mixture. Suitable classes of solvents include alkanes, halogenated alkanes, alkenes, alcohols, ketones, nitriles, ethers, esters, and mixtures thereof. Especially preferred solvents include acetone, methyl ethyl ketone, acetonitrile, methanol, ethanol, isopropyl ether, t-butyl methyl ether (TBME), tetrahydrofuran (THF), and mixtures thereof. Water content relative to the amount of solvent, on a volume-for-volume basis, may range from about 0.1 to about 50 vol %. In the case of acetone and water mixtures, the preferred water content is from about 0.1 to about 30 vol %. The concentration of γ-CD in the liquid mixture should be in the range of from about 5 to about 50 g/100 ml.

Once the enantiomerically-enriched liquid phase is established it may be separated from the solid phase by filtration and further treated to obtain further enantiomeric enrichment. It was discovered that there is a substantial disparity in the solubilities of the pure enantiomer and a racemic mixture of DCPN, with the pure form exhibiting much higher solubility than the racemic mixture. Accordingly, one may take advantage of this fact by evaporating solvent from the recovered liquid phase to obtain a solid mixture that contains both racemic DCPN and one of the two pure enantiomers. This solid mixture may then be contacted with sufficient solvent to selectively dissolve up to 95 wt % of the solid mixture. The amount of solvent used is readily calculable from the degree of enantiomeric enrichment and from the amount of and solubility of the pure enantiomer present in the solid mixture. Preferred solvents include methanol, ethanol, hexane, TBME, diisopropyl ether (DIPE) and mixtures of acetone and water.

EXAMPLES 1-15

A solid racemic mixture of the enantiomers of 4-(3,4-dichlorophenyl)-3,4-dihydro-1(2H)-naphthalenone was dissolved in a miscible solvent and water mixture at room temperature. Solid, substantially pure, unsupported γ-CD in the form of powder was then added to the liquid mixture and the same was stirred vigorously for about one hour with a motorized stir paddle, which caused the γ-CD to be in suspension while the stirring took place. Although cyclodextrin is normally soluble in water, the presence of the organic solvent rendered the γ-CD insoluble in the water/solvent mixture. The solid γ-CD particles were then separated from the liquid mixture by centrifuge (except in the cases of use of acetone as the solvent, which did not require centrifugation). The liquid phase was then analyzed by chiral High Pressure Liquid Chromatography (HPLC), and in all cases found to have been enriched in the (+) or R-enantiomer. The (−) or S-enantiomer was either recovered from the γ-CD by solvent extraction or the amount thereof simply calculated by mass balance. Table 1 shows the solvents used, the water content (vol % based upon ml water per ml solvent), and the concentrations of γ-C ([CD]). The same Table shows the results in terms of the concentrations of enantiomer in the liquid mixture, both initially and at equilibrium ([DCPN]), enantiomeric excess (ee) of the (+)-enantiomer in the liquid mixture and of the (−)-enantiomer in the solid γ-CD phase, and a ratio of the enantiomers (Alpha), where Alpha is defined by the expression $$\frac{(100 + \% ee (+) \text{ in liquid}) (100 + \% ee (-) \text{ in solid})}{(100 - \% ee (+) \text{ in liquid}) (100 - \% ee (-) \text{ in solid})}.$$

EXAMPLES 16-21

The procedure of Examples 1-15 was repeated, with the exception that water content was limited to a concentration that was less than or equal to the solubility limit of water in the solvent, thus rendering the solvent miscible in the water. The γ-CD was again obviously insoluble in this liquid phase. The reactants, conditions and results are reported in Table 2.

TABLE 1

| Ex. No. | Solvent | H₂O Content (%) | [CD] (g/100 ml) | [DCPN] (mM) | | ee (%) | | Alpha |
|---|---|---|---|---|---|---|---|---|
| | | | | Initial | Equilibrium | Liquid (+) | Solid (−) | |
| 1 | isopropanol | 12 | 10 | 34.5 | 26.0 | 5.0 | 15.3 | 1.5 |
| 2 | acetonitrile | 16 | 10 | 64.1 | 9.8 | 7.5 | 1.4 | 1.2 |
| 3 | ethanol | 5 | 10 | 46.2 | 20.8 | 5.7 | 4.7 | 1.2 |
| 4 | methanol | 1 | 5 | 5 | 1.6 | 8.7 | 1.1 | 1.2 |
| 5 | THF | 5 | 15 | 100 | 88.9 | 3.5 | 28.0 | 1.9 |
| 6 | THF | 20 | 15 | 100 | 81.6 | 5.3 | 23.5 | 1.8 |
| 7 | THF | 30 | 15 | 100 | 71.6 | 7.0 | 17.6 | 1.6 |
| 8 | THF | 30 | 15 | 140 | 101.9 | 5.4 | 14.4 | 1.5 |
| 9 | THF | 30 | 10 | 100 | 76.9 | 5.3 | 17.6 | 1.6 |
| 10 | THF | 30 | 40 | 100 | 40.8 | 13.5 | 9.3 | 1.6 |
| 11 | acetone | 10 | 10 | 10 | 5.3 | 11.6 | 13.1 | 1.6 |
| 12 | acetone | 10 | 10 | 50 | 28.6 | 11.2 | 15.0 | 1.7 |
| 13 | acetone | 10 | 10 | 100 | 68.6 | 8.2 | 17.9 | 1.7 |
| 14 | acetone | 7.5 | 10 | 100 | 87.7 | 2.7 | 19.0 | 1.6 |

TABLE 1-continued

| Ex. No. | Solvent | H₂O Content (%) | [CD] (g/100 ml) | [DCPN] (mM) Initial | [DCPN] (mM) Equilibrium | ee (%) Liquid (+) | ee (%) Solid (−) | Alpha |
|---|---|---|---|---|---|---|---|---|
| 15 | acetone | 5 | 10 | 100 | 97.8 | 2.1 | 93 | 28.0 |

TABLE 2

| Ex. No. | Solvent | H₂O Content (%) | [CD] (g/100 ml) | [DCPN] (mM) Initial | [DCPN] (mM) Equilibrium | ee (%) Liquid (+) | ee (%) Solid (−) | Alpha |
|---|---|---|---|---|---|---|---|---|
| 16 | TBME | 0.2 | 5 | 5.0 | 4.7 | 1.7 | 6.3 | 1.2 |
| 17 | TBME | 0.5 | 5 | 5.0 | 4.1 | 4.5 | 11.2 | 1.4 |
| 18 | TBME | 1.0 | 5 | 5.0 | 3.4 | 7.6 | 11.0 | 1.5 |
| 19 | isopropyl ether | 1.0 | 5 | 5.0 | 3.7 | 3.2 | 5.0 | 1.2 |
| 20 | methylethyl ketone | 1.0 | 5 | 5.0 | 3.7 | 4.8 | 3.5 | 1.2 |
| 21 | 50/50 ethanol/hexane | 1.0 | 5 | 5.0 | 3.8 | 2.4 | 2.4 | 1.1 |

EXAMPLES 22-26

A solid racemic mixture of the enantiomers of DCPN was dissolved in the solvent TBME to a concentration of 100 mM, then added to an equal volume of water, so that the vol % of water, based upon ml water per ml solvent, was 100%. Because water was present in a concentration that was greater than its saturation concentration in the solvent, the water/solvent mixture became nonhomogeneous, separating into two phases. Gamma-cyclodextrin granules were than added, followed by the stirring, analysis and recovery steps of previous Example. However, since the solvent was fairly uniformly distributed in the water by the stirring, the water/solvent mixture still constituted a homogeneous single phase. It was apparent that the γ-CD did not dissolve in either of the two phases. The results are shown in Table 3.

TABLE 3

| Ex. No. | [CD] (g/100 ml) | [DCPN] (mM) Initial | [DCPN] (mM) Equilibrium | ee (%) Liquid (+) | ee (%) Solid (−) | Alpha |
|---|---|---|---|---|---|---|
| 22 | 5 | 5 | 3.0 | 12.1 | 9.0 | 1.5 |
| 23 | 15 | 30 | 5.9 | 18.8 | 4.6 | 1.6 |
| 24 | 15 | 100 | 42.7 | 16.6 | 12.4 | 1.8 |
| 25 | 15 | 150 | 89.9 | 9.4 | 14.1 | 1.6 |
| 26 | 30 | 30 | 4.9 | 20.0 | 3.9 | 1.6 |

EXAMPLES 27-39

Solvents were used to selectively extract pure (+)-enantiomer of DCPN from partially enriched solid mixtures containing both pure (+)-enantiomer and racemic mixtures. With respect to Examples 27-32 and 36-39, such solid mixtures were obtained by evaporating solvent from the liquid phases obtained in extractions of the type set forth in the foregoing Examples. With respect to Examples 33-35, the solid mixtures were simulated partially enriched solid mixtures obtained from 90 wt % racemic DCPN and 10 wt % 100% ee of the (+)-enantiomer of DCPN. The results are shown in Table 4. In Table 4, the initial degree of enantiomeric enrichment is indicated by "Start %ee," the final degree of enantiomeric enrichment obtained is indicated by "End % ee," while "ace" is an abbreviation for acetone. "Solvent volume" was measured in mls of solvent per 0.25 g of solid.

TABLE 4

| Ex. No. | Start % ee (+) | Solvent | Solvent Volume (ml) | Racemic [DCPN] (mm) | (+) [DCPN] (mm) | End % ee (+) | % Recovery Pure (+) |
|---|---|---|---|---|---|---|---|
| 27 | 9.1 | hexane | 5 | 8.9 | 8.7 | 49.5 | 55.4 |
| 28 | 9.1 | methanol | 3 | 25.7 | 15.3 | 37.4 | 58.6 |
| 29 | 9.1 | ethanol | 3 | 57.2 | 15.3 | 36.5 | 58.5 |
| 30 | 9.1 | 90/10 ace/H₂O | 1 | 85.9 | 77.7 | 47.5 | 100 |
| 31 | 9.1 | 80/20 ace/H₂O | 3 | 58.6 | 27.9 | 32.2 | 100 |
| 32 | 9.1 | 85/15 ace/H₂O | 2.5 | 89.3 | 33.9 | 27.5 | 100 |
| 33 | 10 | DIPE | 1 | 24.6 | 83.2 | 77 | 96.5 |
| 34 | 10 | ethanol | 1 | 24.4 | 81.6 | 77 | 94.7 |
| 35 | 10 | hexane | 1 | 5.8 | 23.0 | 80 | 26.0 |
| 36 | 10 | TBME | 0.5 | 87.8 | 143 | 62 | 83.1 |
| 37 | 7.9 | ethanol | 1 | 28.0 | 35.3 | 56 | 51.9 |
| 38 | 7.9 | hexane | 2.2 | 6.0 | 10.7 | 64 | 34.6 |

TABLE 4-continued

| Ex. No. | Start % ee (+) | Solvent | Solvent Volume (ml) | Racemic [DCPN] (mm) | (+) [DCPN] (mm) | End % ee (+) | % Recovery Pure (+) |
| --- | --- | --- | --- | --- | --- | --- | --- |
| 39 | 9.7 | ethanol | 1.3 | 45.2 | 32.8 | 50 | 48.7 |

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A method for separation of enantiomers of 4-(3,4-dichlorophenyl)-3,4-dihydro-1(2H)-naphthalenone comprising the steps of:
   (a) contacting said enantiomers with a liquid mixture of water and a solvent, said liquid mixture containing a substantially pure and unsupported binding substance selected from γ-cyclodextrin, anionic poly-γ-cyclodextrin (2-hydroxypropyl)-γ-cyclodextrin, γ-cyclodextrin phosphate sodium salt, succinylated-γ-cyclodextrin, octakis (2,3,6-tri-O-acetyl)-γ-cyclodextrin, and carboxymethyl-γ-cyclodextrin, thereby selectively binding one of said enantiomers to said binding substance; and
   (b) separating said binding substance from said liquid mixture wherein said enantiomers are soluble in said liquid mixture to at least 1.0 mM and said solvent is selected from the group consisting essentially of alkanes, halogenated alkanes, alkenes, alcohols, ketones, nitriles, ethers, esters, and mixtures thereof and is selected so as to render said binding substance substantially insoluble in said liquid mixture.

2. The method of claim 1 wherein said selectively bound enantiomer is recovered from said separated binding substance.

3. The method of claim 2 wherein said selectively bound enantiomer is recovered from said separated binding substance by solvent extraction.

4. The method of claim 1 wherein said enantiomer that is not selectively bound is recovered from said liquid mixture.

5. The method of claim 1 wherein said liquid mixture is homogeneous.

6. The method of claim 5 wherein said solvent in said homogeneous liquid mixture is miscible with water.

7. The method of claim 5 wherein said solvent in said homogeneous liquid mixture is immiscible with water and water is present in a concentration less than or equal to its saturation concentration in said solvent.

8. The method of claim 1 wherein said liquid mixture is nonhomogeneous and said water is present in a concentration greater than its saturation concentration in said solvent.

9. The method of claim 1 wherein step (a) is conducted by agitation.

10. The method of claim 9 wherein said agitation is conducted by stirring.

11. The method of claim 1 or 3 wherein said solvent is acetone.

12. The method of claim 1 or 3 wherein said solvent is t-butyl methyl ether.

13. The method of claim 1 or 3 wherein said solvent is tetrahydrofuran.

14. The method of claim 1 wherein the water content of said liquid mixture is from 0.1 to 50 vol %.

15. The method of claim 1 wherein the concentration of said binding substance in step (a) is from 5 to 50 g/100 ml.

16. A chemical complex of enantiomers of 4-(3,4-dichlorophenyl)-3,4-dihydro-1(2H)-naphthalenone and a binding substance selected from γ-cyclodextrin, anionic poly-γ-cyclodextrin, (2-hydroxypropyl)-γ-cyclodextrin, γ-cyclodextrin phosphate sodium salt, succinylated-γ-cyclodextrin, octakis (2,3,6-tri-O-acetyl)-γ-cyclodextrin, and carboxymethyl-γ-cyclodextrin.

17. The complex of claim 16 wherein the degree of enrichment in the (−)-enantiomer is from 1 to 99%.

18. A method of improving the enantiomeric excess of a solid mixture of enantiomers of 4-(3,4-dichlorophenyl)-3,4-dihydro-1(2H)-naphthalenone that has been enriched in one enantiomer comprising contacting said mixture with sufficient solvent to selectively dissolve up to 95 wt % of said mixture wherein said solvent is selected from methanol, ethanol, acetone, hexane, t-butyl methyl ether, diisopropyl ether, and mixtures of acetone and water.

19. The method of claim 18 wherein the amount of water in said mixtures of acetone and water is from 0.1 to 30 vol %.

* * * * *